United States Patent [19]

Brunnee

[11] 4,376,391
[45] Mar. 15, 1983

[54] DEVICE FOR PREPARING DISSOLVED SUBSTANCES FOR MASS-SPECTROMETRIC ANALYSIS

[75] Inventor: Curt Brunnee, Platjenwerbe, Fed. Rep. of Germany

[73] Assignee: Finnigan Mat GmbH, Bremen, Fed. Rep. of Germany

[21] Appl. No.: 238,280

[22] Filed: Feb. 25, 1981

[30] Foreign Application Priority Data

Feb. 28, 1980 [DE] Fed. Rep. of Germany ....... 3007538

[51] Int. Cl.³ .......................................... G01N 35/02
[52] U.S. Cl. ............................. 73/863.12; 73/864.81; 250/288; 422/64; 422/101
[58] Field of Search ................ 73/61 R, 61.1 R, 61.3, 73/864.81; 250/288; 422/78, 101, 244

[56] References Cited

U.S. PATENT DOCUMENTS

| | | | |
|---|---|---|---|
| 2,702,479 | 2/1955 | Black et al. | 250/288 |
| 3,188,180 | 6/1965 | Hollev | 422/78 |
| 3,586,488 | 6/1971 | Trevalion et al. | 73/863.12 |
| 3,751,660 | 8/1973 | Thurston | 73/864.81 |

*Primary Examiner*—S. Clement Swisher
*Attorney, Agent, or Firm*—Sughrue, Mion, Zinn, Macpeak and Seas

[57] ABSTRACT

A fraction obtained from a liquid chromatograph column is introduced into a cup-shaped collecting vessel 12 having a centrally apertured funnel-shaped bottom surface 14. A sample holder 13 is removably accommodated in the aperture, and after the evaporation of the fraction solvent the remaining residue 11 collects on or in the holder, which may then be removed and directly introduced into the ionization chamber of a mass spectrometer for further analysis.

15 Claims, 8 Drawing Figures

DEVICE FOR PREPARING DISSOLVED SUBSTANCES FOR MASS-SPECTROMETRIC ANALYSIS

BACKGROUND OF THE INVENTION

The invention relates to a device for preparing substances, dissolved in solvent, for mass-spectrometric or similar analysis thereof, it being possible, after removal (evaporation) of the solvent, for the substance to be introduced by a sample holder of small dimensions into the mass spectrometer (ionisation chamber) or the like, preferably for the mass-spectrometric off-line analysis of fractions spearated in a liquid chromatograph (LC).

It is known and customary practice to combine liquid chromatographs (LC) and mass spectrometers (MS) for a great number of analytical examinations. The fractions, which are separated in the liquid chromatographs, of the substances to be analysed emerge from the LC column in solvents and are collected in vessels. The solvent must be evaporated for the subsequent (mass-spectrometric) analysis. Then, in a further operation the substance (sample) left as a residue is passed into a relatively small crucible (sampel holder) which can be introduced into the ion source of the mass spectrometer. In place of the crucible, a wire or differently designed sample holder can be used to introduce the substance into the mass spectrometer.

To transfer the substance from the collecting vessel of the LC into or onto the sample holder of the mass spectrometer, it is often necessary for the fraction concerned to be dissolved once more in a solvent and for the latter to be subsequently evaporated. This multistage dissolving and evaporating process is necessary due to, on the one hand, the relatively large capacity of the collecting vessel (at least 1 cm$^3$) and, on the other hand, the, in contrast, small dimensions of the sample holder. The fraction emerging from the LC is normally yielded in a strongly diluted form so that the collecting vessel must be correspondingly dimensioned for this purpose.

SUMMARY OF THE INVENTION

The object underlying the invention is to propose a device for transferring substances, contained in solvents, into a mass spectrometer or the like, which device makes it possible in a simple manner to transfer the substance in question, after evaporation of the solvent, to a sample holder of relatively small dimensions.

To achieve this object, the device according to the invention is characterised in that the substance (fraction) present in the solvent is received in a relatively large-dimensioned collecting vessel which, after removal of the solvent, can be reduced in size to a sample holder, which can be introduced directly into the mass spectrometer and which receives the substance left in the form of a residue.

The concept underlying the invention is accordingly to use the collecting vessel, in which the dissolved substance is received, directly as a sample holder and, accordingly, to avoid "decanting" of the substance. This concept is advantageously embodied in that the sample holder, which can be introduced into the mass spectrometer, forms part of the (large-capacity) collecting vessel for the dissolved fraction.

For this purpose the collecting vessel and smaple holder can be designed in different ways. The former is funnel-shaped, preferably at least in its lower section, a sample holder being inserted into an opening of the collecting vessel and forming a part of the said vessel, at the lowest point thereof. When the solvent is evaporated, the substance is collected in the area of the sample holder inside the collecting vessel. The sample holder can then be removed, together with the sample, from the collecting vessel and introduced directly into the mass spectrometer (ion source).

The sample holder can in this case be designed in different ways, for example with a funnel-shaped recess for the substance, in the form of a substantially flat plate or with a wire which projects upwards and therefore extends into the collecting vessel and which acts as a carrier for the substance. The latter can in this case optionally be heatable or can be in the form of an "activated" emitter wire for carrying out field desorption.

The invention is particularly advantageous and suitable as a result of magazines being used as devices for automatic transfer of samples to a mass spectrometer or the like. A sample magazine is in this case designed in accordance with the invention so that the separation of the sample holder from the remaining part of the collecting vessel takes place inside the said sample magazine. This is done for example by designing the sample magazine with two magazine discs which can be moved relative to one another and cause the parts of the collecting vessel to be separated by moving apart.

BRIEF DESCRIPTION OF THE DRAWINGS

Exemplary embodiments of the invention are explained in more detail below with the aid of the drawings.

In the drawings

DETAILED DESCRIPTION OF THE PREFERRED EMBODIMENTS

A substance 11, which emerges for example from the column of a liquid chromatograph (not shown) and is dissolved in a solvent 10, is collected in a relatively large-capacity collecting vessel 12. The latter has a receiving capacity of at least approximately 1 cm$^3$. The solvent 10 is then evaporated in the said collecting vessel 12 so that the substance 11, which is to be analysed for example in a mass spectrometer (not shown) is left as a residue in the collecting vessel 12.

A sample holder 13 of relatively small dimensions is arranged inside the collecting vessel 12 or forms a part thereof. The design of the said sample holder 13 and its position relative to the collecting vessel 12 are such that, when or after the solvent 10 is evaporated, the substance 11 is left as a residue in or on the sample holder 13. The said sample holder can then be introduced directly into the mass spectrometer or into an ionisation chamber thereof.

Figure 1:
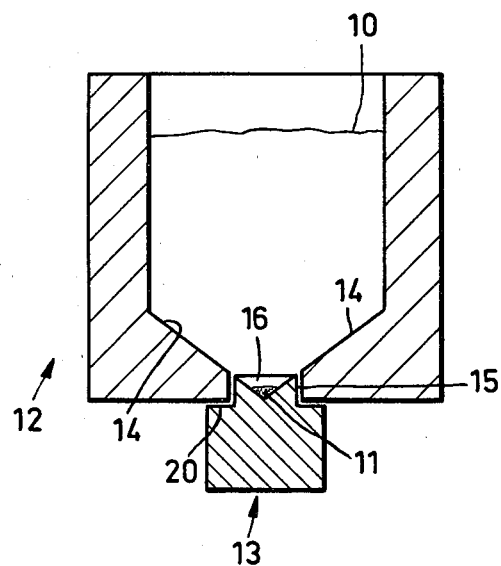
FIG. 1 shows, in vertical section, a collecting vessel having a sample holder designed as a part thereof.

In the exemplary embodiment according to FIG. 1, the lower section of the collecting vessel 12 is funnel-shaped as a result of having a converging inner bottom face 14. At the lowest point on the bottom face 14, which point is central in the present case, the collecting vessel 12 forms an opening 15. The sample holder 13 fits into the said opening in such a way that the bottom face 14 is completed by the upper side of the sample holder 13. In the exemplary embodiment according to FIGS. 1 and 2, the funnel-shaped bottom face 14 is continued in a likewise funnel-shaped recess 16 on the upper side of the sample holder 13. As a result, in the arrangement according to FIG. 1, the lower part of the interior of the collecting vessel 12 is generally funnel-shaped in such a way that, upon evaporation of the solvent 10, the substance 11 automatically collects in the area of the recess 16 and therefore at the desired place on the sample holder 13. As a result of the recess 16, the said sample holder acts in principle like a known crucible for further processes, i.e. like a sample holder having a recess for receiving the substance.

Figure 2:
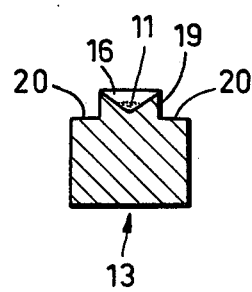
FIG. 2 shows, also in vertical section, the sample holder as an individual part removed from the collecting vessel above.
Figure 3:
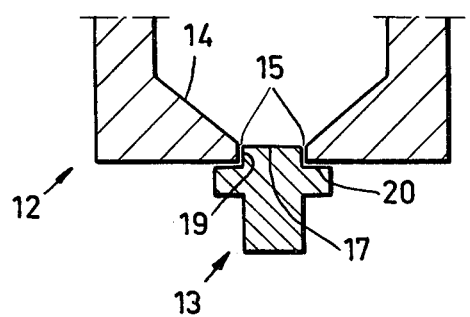
FIG. 3 shows, also in vertical section, the lower part of a collecting vessel having an alternative type of sample holder.

In the alternative according to FIG. 3, the sample holder 13 is of substantially flat form in the section receiving the substance 11. The sample holder 13 acts in this case as a plate 17 which, however, similarly to the exemplary embodiment according to FIGS. 1 and 2, is adjacent to the bottom face 14 of the collecting vessel 12 in the area of the lowest point thereon.

Figure 4:
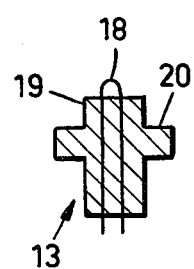
FIG. 4 shows, as a detail, a sample holder with a wire.

Similary, the sample holder according to FIG. 4 is attached to a collecting vessel 12 in such a way that a wire 18, which is in the form of a loop, spiral or of similar design, projects into the collecting vessel 12. In this case also, the arrangement relative to the collecting vessel 12 is such that the substance 11 collects at or on the wire 18 upon evaporation of the solvent 10.

Therefore, virtually all the known conventional types of sample holders can be used in the described sense when they are correspondingly designed. This makes it also possible to use various (known) ionisation processes. For example, the wire 18 can be heated (electrically) in order that the sample may be evaporated in the ionisation chamber in this way. Such a solution (heatisng for evaporation) can also be implemented with regard to the sample holders 13 according to FIGS. 1 to 3. However, through "activation" the wire 18 can also be provided with a large number of tips which make it possible to carry out field desorption as an ionisation process.

The sample holders 13 are designed so that they can be positively connected to and fitted on the collecting vessel 12 in the area of the opening 15. For this purpose the sample holders 13 shown in this case are provided with a projection 19 which is limited by a ledge and which fits into the correspondingly formed opening 15 of the collecting vessel 12. A shoulder 20, which is connected to the said projection, on the sample holder 13 abuts on the flat underside of the collecting vessel 12.

Moreover, the collecting vessel 12 and the sample holder 13 also can be made of different materials in such a way that they are optimally adapted to each field of used.

The collecting vessels 12 which are designed in the manner described can be used particularly for the automatic transfer of samples using magazines. An example of a suitable sample magazine 21 is illustrated in FIGS. 5 to 8.

The sample magazine 21 is in the present case in the form of a rotating disc. The collecting vessels 12 are received in an upper magazine disc 22. For this purpose, the said magazine disc is provided along its periphery with suitable holders in the form of through-holes 23, each serving to receive a collecting vessel 12. The upper sections of the collecting vessel 12 are provided for this purpose with supporting flanges 24 which rest on the magazine disc 22.

The collecting vessels 12 pass through the magazine disc 22 in such a manner that, in the starting position (FIG. 5), the sample holders 13 rest on a second lower magazine disc 25. The position of the magazine discs 22 and 25 relative to one another is such that collecting vessels 12 and sample holders 13 are kept in a sealing contact with one another. The lower magazine disc 25 is provided for this purpose with cup-shaped recesses 26 which correspond to the holes 23 of the magazine disc 22. The lower parts of the sample holders 13 are received in the recesses 26, that is, while being supported on a flexible base which in this case is in the form of a compression spring 27.

Figure 5:
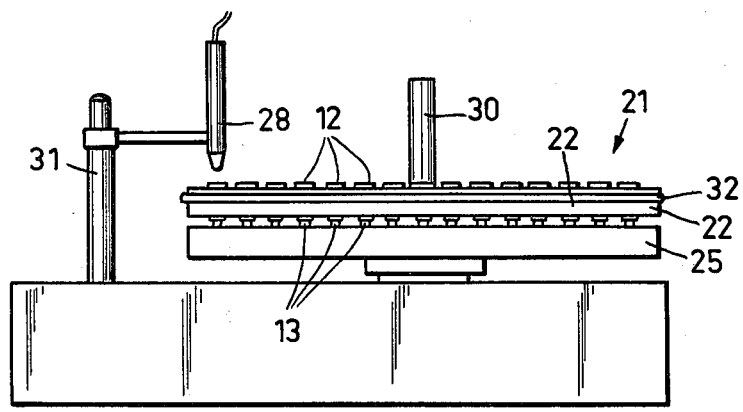
FIG. 5 shows, as a diagrammatic side view, a magazine for receiving a relatively large number of collecting vessels in the receiving position.

In the starting position according to FIG. 5, the liquid (solvent and substance) emerging from an LC is introduced into the collecting vessels 12 by a filling device 28 connected to the LC. For this purpose the sample magazine 21 is rotated cyclically by a stepping motor 29 which acts on a driving shaft 30 carrying the magazine discs 22 and 25. The filling device 28, which is pivotably mounted on a supporting column 31, is in this case pivoted into a position above the magazine discs 22, 25.

Figure 6:
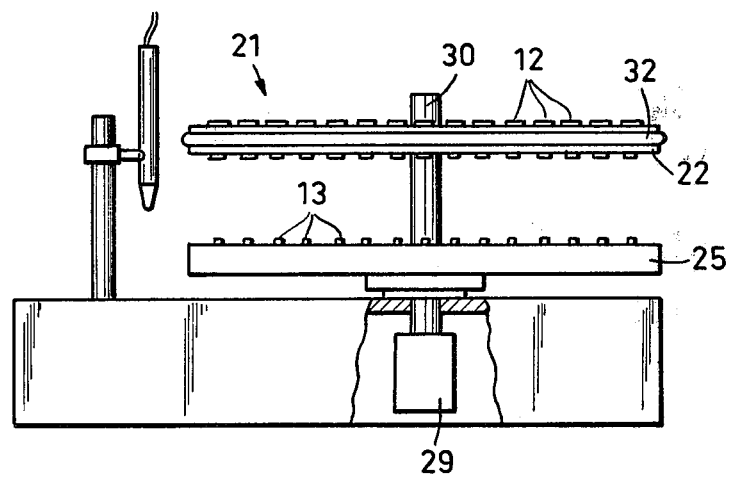
FIG. 6 shows the sample magazine according to FIG. 5 in the position for separating the collecting vessel and sample holder.
Figure 7:
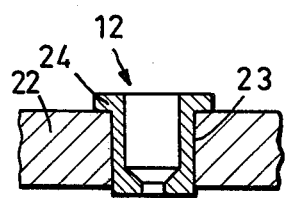
FIG. 7 shows a detail of the collecting vessel in FIG. 6, on an enlarged scale.
Figure 8:
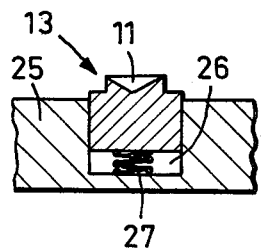
FIG. 8 shows a detail of the sample holder in FIG. 6, also on an enlarged scale.

After the collecting vessels 12 of the sample magazine 21 are filled, the filling device 28 is pivoted into a lateral position (FIG. 6). Then the upper magazine disc 22 is moved upwards, i.e. is separated from the lower magazine disc 25. As a result, the collecting vessels 12 are separated from the sample holders 13 retained on the magazine disc 25. The sample holders 13 provided with the samples can now be appropriately removed from the sample magazine 21, namely the magazine disc 25.

The sample magazine 21, namely the upper magazine disc 22, can be heated. A heating system 32, (electrical heating or a flowing heating medium), which is arranged in the area of the outer periphery and extends around the magazine disc, is provided in the present exemplary embodiment. The said heating system causes the solvent 10 to be evaporated or the evaporation to be accelerated.

I claim:

1. Device for preparing fractions separated in a liquid chromatograph including substances dissolved in solvents for mass-spectrometric analysis after evaporation of the solvents by direct introduction into an ionization chamber of a mass spectrometer comprising: a relatively large dimensioned collecting vessel (12) adapted to hold a separated fraction, and a relatively small dimensioned sample holder (13) removably disposed within said collecting vessel and forming a portion of the inner surface thereof, whereby the sample holder and any substance (11) left therein in the form of a residue after solvent evaporation may be removed from the collecting vessel and directly introduced into a mass spectrometer for further analysis.

2. Device according to claim 1, wherein the sample holder is detachably mounted in a lower section of the collecting vessel.

3. Device according to claim 2, wherein the sample holder extends into a central bottom opening (15) of the collecting vessel.

4. Device according to claim 3, wherein the collecting vessel has a converging, funnel-shaped bottom face (14).

5. Device according to claim 4, wherein the sample holder is provided with a means for receiving a residue substance.

6. Device according to claim 5, wherein the upper side of the sample holder has a funnel-shaped recess (16) which acts as a continuation and lowest termination of the correspondingly shaped bottom face of the collecting vessel.

7. Device according to claim 5, wherein the means for receiving the substance is in the form of a flat plate (17).

8. Device according to claim 5, wherein the means for receiving the substance is in the form of a wire loop (18).

9. Device according to claim 8, wherein the collecting vessel and the sample holder are made of different materials.

10. Device according to claim 9, wherein the sample holder has a projection (19) which fits into the opening of the collecting vessel.

11. Device according to claim 1, wherein a plurality of collecting vessels are disposed in a rotating sample magazine (21) from which a corresponding plurality of sample holders can be separated in order to be introduced into a mass spectrometer.

12. Device according to claim 11, wherein the sample holders of all the collecting vessels of the sample magazine can be detached conjointly.

13. Device according to claim 11 or 12, wherein the sample magazine comprises two magazine discs (22, 25), one of which accommodates the collecting vessels and the other of which accommodates the sample holders (13), and wherein the collecting vessels and sample holders may be separated by movement of the magazine discs relative to one another.

14. Device according to claim 13, wherein the magazine discs are arranged one above the other so as to be movable up and down on a common vertical drive shaft (30), the upper magazine disc (22) accommodating the collecting vessels in through-holes (23) and the lower magazine disc (25) accommodating the sample holders in recesses (26).

15. Device according to claim 14, wherein the upper magazine disc is provided with a heating system (32) arranged along the outer periphery thereof.

* * * * *